United States Patent [19]

Deeg et al.

[11] Patent Number: 4,645,739

[45] Date of Patent: Feb. 24, 1987

[54] PROCESS AND REAGENT FOR THE DETERMINATION OF N-CARBAMOYLSARCOSINE WITH THE USE OF A NEW ENZYME

[75] Inventors: Rolf Deeg, Bernried; Albert Röder, Seeshaupt; Joachim Siedel, Bernried; Helmgard Gauhl, Tutzing; Joachim Ziegenhorn, Starnberg, all of Fed. Rep. of Germany

[73] Assignee: Boehringer Mannheim GmbH, Mannheim Waldhof, Fed. Rep. of Germany

[21] Appl. No.: 562,072

[22] Filed: Dec. 16, 1983

[30] Foreign Application Priority Data

Dec. 27, 1982 [DE] Fed. Rep. of Germany ....... 3248145

[51] Int. Cl.[4] .................. C12Q 1/26; C12Q 1/00; C12Q 1/34; C12Q 1/28
[52] U.S. Cl. ........................................ 435/25; 435/4; 435/18; 435/28; 435/195; 435/228; 435/810; 435/814; 435/815; 435/816; 435/822; 435/830; 435/859
[58] Field of Search ............... 435/4, 18, 25, 28, 195, 435/228, 810, 814, 815, 816, 822, 830, 859

[56] References Cited

U.S. PATENT DOCUMENTS

3,806,420  4/1974  Holz et al. .................... 435/231
4,039,384  8/1977  Suzuki et al. ................. 435/227

FOREIGN PATENT DOCUMENTS

0083297  5/1982  Japan ................................ 435/28

OTHER PUBLICATIONS

Trinder, *Ann. Clin. Biochem.*, 6 (1969) pp. 24–27.
*Enzyme Nomenclature*, 1973, Elsevier Publishing Co. Inc., N.Y., pp. 252–253.

*Primary Examiner*—Robert J. Warden
*Assistant Examiner*—Patricia Kate White
*Attorney, Agent, or Firm*—Felfe & Lynch

[57] ABSTRACT

The present invention provides a process for the determination of N-carbamoylsarcosine, wherein a sample solution containing N-carbamoylsarcosine is reacted with N-carbamoylsarcosine-amidohydrolase to give sarcosine, which is then determined.

The present invention also provides the enzyme N-carbamoylsarcosine-amidohydrolase, a process for obtaining it and a reagent containing it.

12 Claims, No Drawings

PROCESS AND REAGENT FOR THE DETERMINATION OF N-CARBAMOYLSARCOSINE WITH THE USE OF A NEW ENZYME

The present invention is concerned with a process and a reagent for the determination of N-carbamoylsarcosine with the use of a enzyme, N-carbamoylsarcosine-amidohydrolase, and is also concerned with obtaining this enzyme.

We have found that micro-organisms possess the ability to convert creatinine into N-carbamoylsarcosine. For the investigation of this breakdown path, a specific process would be desired for the determination of N-carbamoylsarcosine. Furthermore, such a process could also be employed for the determination of creatinine itself by a previous conversion thereof into N-carbamoylsarcosine.

Therefore, it is an object of the present invention to provide a process for the specific determination of N-carbamoylsarcosine.

Thus, according to the present invention, there is provided a process for the determination of N-carbamoylsarcosine, wherein a solution containing N-carbamoylsarcosine is reacted with N-carbamoylsarcosine-amidohydrolase to give sarcosine which is then determined.

The present invention is based upon the discovery of the new enzyme N-carbamoylsarcosine-amidohydrolase, abbreviated CSH, which forms sarcosine specifically, with the splitting off of carbon dioxide and ammonia according to the following equation:

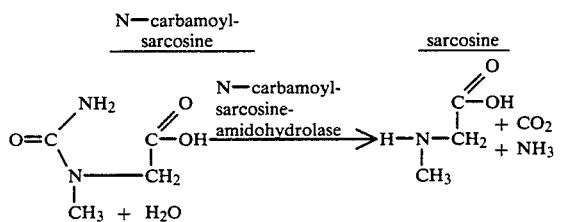

Sarcosine formed by the process according to the present invention can be determined by known methods, for example with the use of sarcosine dehydrogenase and measurement of NADH formed or by means of sarcosine oxidase and measurement of hydrogen peroxide formed or of oxygen consumed. The determination with the use of sarcosine oxidase and measurement of the hydrogen peroxide formed is preferred. The latter can be determined not only titrimetrically but also potentiometrically, polarographically and colorimetrically, as well as enzymatically. Amongst these, there are preferred the enzymatic methods using catalase or peroxidase (POD) since these are extremely specific and dependable. The determination by means of catalase takes place in the presence of a β-diketone, for example acetylacetone, and methanol, ethanol or methylene glycol. The determination with peroxidase takes place in the presence of one or more chromogens. Examples of appropriate chromogens include 2,2'-aminobenzthiazoline-sulphonic acid (ABTS), the indicator system according to Trinder (Ann. Clin. Biochem., 6, 24–27/1969) in which phenol or another aromatic alcohol or aromatic amine is oxidatively coupled with 4-aminophenazone or with a 4-aminophenazone derivative to give a coloured material. Appropriate aromatic alcohols or amine include, for example, p-chlorophenol, aminophenols, naphthol and its derivatives, naphthylamine and its derivatives, aminoquinolines, hydroxyquinolines, dihydroxyphenyl-acetic acid and the like. Instead of 4-aminophenazone, there can be used appropriate 4-aminophenazone derivatives, phenylenediamine-sulphonic acid, methylbenzothiazolohydrazone (MBTH), sulphonated methylbenzothiazolohydrazone (S-MBTH) and derivatives thereof.

The determination process according to the present invention for N-carbamoylsarcosine is preferably carried out in a buffered solution, the preferred pH value being from about 6 to 9.

The present invention also provides a reagent for the determination of N-carbamoylsarcosine, which contains N-carbamoylsarcosine-amidohydrolase and a system for the detection of sarcosine.

A preferred reagent of the above-indicated type contains, as the system for the detection of sarcosine, sarcosine oxidase, peroxidase and a chromophore.

A further preferred system for the detection of sarcosine consists of sarcosine dehydrogenase and NAD.

The reagents according to the present invention can also contain a buffer (pH 6 to 9) and possibly a surface-active agent.

The present invention also provides the enzyme N-carbamoylsarcosine-amidohydrolase (CSH).

The following properties have been determined for this enzyme:

STABILITY

Stability optimum: pH 6 to 6.5; good stability properties are present in phosphate buffer, the best stability being achieved by the addition of glycerol.

Heating of CSH 20 mg./ml. in 50% glycerol, pH 6.5, for 20 minutes:

residual activity %:
40° C./100
50° C./48
60° C./24
80° C./0

At +4° C. in 50% glycerol, 100% activity is maintained after 4 weeks.

SPECIFICITY

Creatinine, creatine, sarcosine, N-methylhydantoin and hydantoin are not reacted. Michaelis constants for N-carbamoylsarcosine at 25° C., pH 8.0, 0.1M/liter tris buffer: 3.3 to $3.8 \times 10^{-3}$M; in 0.1M/liter potassium pyrophosphate buffer, pH 8.5: 5.0 to $7.1 \times 10^{-3}$M.

pH OPTIMUM

The pH optimum depends upon the buffer substance. In the case of potassium pyrophosphate buffer, it was found to be 8.5 and in the case of tris buffer and hopes buffer was found to be 8.0.

MOLECULAR WEIGHT

MW about 40,000. Determination by disc electrophoresis.

INHIBITORS

5 μg. merthiolate/ml. inhibits up to 95%.

EQUILIBRIUM

The equilibrium was determined with 0.5 U/ml. CSH in 90 mM/liter tris buffer, pH 8.0:

$$\frac{\text{Sarcosine}}{\text{N—carbamoylsarcosine}} = \frac{12.5 \text{ mM}}{<0.001 \text{ mM}} = >1 \times 10^4$$

CSH is obtained by culturing appropriate microorganisms and obtaining the enzyme from the biomass or from the culture broth. Especially preferred microorganisms include those of the genus Arthrobacter, Micrococcus and Moraxella, the best results having been achieved with Arthrobacter DSM 2563, DSM 2564, Micrococcus spec. DSM 2565 and Moraxella DSM 2562.

The micro-organisms can be used in the form of a cell suspension for the determination process according to the present invention. However, it is preferable to use a purified enzyme preparation. This can be prepared by digesting a micro-organism which has been cultured on N-methylhydantoin and which has a sufficiently high content of N-carbamoylsarcosine-amidohydrolase to make working up worthwhile, followed by separating off insoluble material. The digestion can be carried out by using conventional methods, such as high pressure dispersion, ultrasonics, disintegration mills or lysozyme addition. The clear extract obtained is mixed with 0.3 to 0.5% by weight of polyethyleneimine, the precipitate formed is separated off and the supernatant is diluted with water, the enzyme thereby precipitating out, whereafter it can be separated off.

For high purification, the so obtained enzyme can be subjected to the usual methods of enzyme high purification. The enzyme preparation produced as described above is preferably dissolved in an appropriate buffer and fractionated at an ammonium sulphate concentration of from 1.3M to 2.2M. Chromatography over phenyl-sepharose and DE-52-cellulose, as well as gel filtration over Sephacryl S 200, gives an enzyme preparation which is free from foreign activities and has a specific activity of 2 U/mg. protein, in a yield of about 70%, referred to the amount of enzyme found to be present in the cell extract. The so obtained enzyme can be stored, without loss of activity, in 50% glycerol/water solution, pH 6.5, at +4° C. for at least six months.

The present invention makes it possible specifically to determine N-carbamoylsarcosine. Such a method is a considerable contribution especially for the elucidation of creatinine metabolism. In combination with the conversion of creatinine into N-carbamoylsarcosine, the process according to the present invention can also be used directly for the determination of creatinine.

The following Examples are given for the purpose of illustrating the present invention:

EXAMPLE 1

Determination of N-carbamoylsarcosine

Principle:

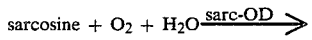

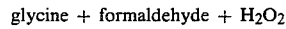

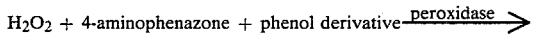

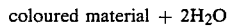

Reagent:

-continued 0.1 mol/liter tris HCl buffer, pH 8
0.2 mmol/liter 4-aminophenazone } colour-forming system
2.0 mmol/liter 2,4,6-tribromo-3-hydroxybenzoate
0.4% Triton X-100 (surface-active agent as solubility improver)
2.0 U/ml. carbamoylsarcosine-amidohydrolase
2.0 U/ml. sarcosine oxidase (sarc-OD)
2.0 U/ml. peroxidase (POD)

Sample

Aqueous solution with 0 to 35.6 μmol/liter N-carbamoylsarcosine.

Test batch 2 ml. reagent
100 μl. sample

Conduction of the Assay (or test)

Mix sample and reagent, leave standing for 30 minutes at ambient temperature, transfer to cuvette and read extinction of the sample against reagent blank at $\lambda = 546$ nm.

Result

There is found to be a linear dependency between the extinction and the N-carbamoylsarcosine concentration in the sample.

EXAMPLE 2

(A)

10 ml. of an N-methylhydantoin-containing medium (composition see below) are inoculated with Arthrobacter DSM 2563, BMTU 2194-1, from a tilt agar culture of the same composition and shaken in 100 ml. Erlenmeyer flasks for about 24 hours at 28° C. and 160 r.p.m. Subsequently, it is further inoculated in an amount of 1% into medium of the same composition so that 500 ml. of this culturing stage are available for a 50 liter fermenter (5 × 1 ml. of the 1st culture in each of 100 ml. per 500 ml. Erlenmeyer flask, 24 hours/28° C. and 160 r.p.m.).

This 500 ml. amount is transferred into 50 liters of medium of the same composition and further fermented in a fermenter equipped with 2 plate stirrers per baffle plate, with 1000 liters air/hour and 500 r.p.m. at 28° C. After 10 to 12 hours, the formation of the N-methylhydantoin-decomposing enzyme commences and continues up to the end of the logarithmic growth phase. After 18 hours of culturing, harvesting takes place. The micro-organisms are separated off in a cooled centrifuge and the biomass is subsequently washed with 0.1M phosphate buffer, again centrifuged and frozen. In this way, from 50 liters of culture, there are obtained about 800 g. biomass.

Medium composition per liter: 7 g. $Na_2HPO_4 \times 2H_2O$, 3 g. $KH_2PO_4$, 0.5 g. $MgSO_4 \times 7H_2O$, 10 g. N-methylhydantoin (sterile filtered), 5 g. yeast extract/Difco, 1 ml. trace solution 1+, 0.1 ml. trace solution 2++, 1 ml. vitamin solution+++ (sterile filtered).

+Trace solution 1

100 mg. $MnCl_2 \times 4H_2O$, 100 mg. $FeCl_3 \times 6H_2O$, 100 mg. $CaCl_2 \times 2H_2O$ are dissolved in 100 ml. double distilled water and sterilised. 1 ml. of this solution is used per liter of medium.

++Trace solution 2

1 mg. $CuCl_2 \times 2H_2O$, 1 mg. of $ZnCl_2$, 1 mg. $(NH_4)_2MoO_4$, 1 mg. $CoCl_2 \times 6H_2O$ are dissolved in 1000 ml. double distilled water and sterilised. 0.1 ml. of this solution is used per liter of medium.

+++Vitamin solution 0.1 mg. biotin, 0.1 mg. pyridoxol, 0.1 mg. pyridoxamine hydrochloride, 0.1 mg. PABS, 1.0 mg. riboflavin, 1.0 mg. nicotinamide, 1.0 mg. folic acid, 10.0 mg. thiamine hydrochloride are dissolved in 100 ml. double distilled water and sterile filtered. 1 ml. of this solution is used per liter of medium.

(B)

The washed cells (1 kg. dry weight) are made up in 50 mM/liter potassium phosphate buffer (pH 6.5) to 15 liters and digested at about 600 bar (ats.) by high pressure dispersion. The cell residue is separated off and the clear extract obtained contains the CSH. It is mixed with 4% by weight of 10% by weight polyethyleneimine (G-35) solution (pH 6.5). After separating off the nucleic acids, the enzyme is precipitated by dilution with water. The small amount of protein precipitate is taken up with 50 mM/liter potassium phosphate buffer (pH 6.5) and fractionated at an ammonium sulphate concentration of from 1.3 to 2.2M/liter. Sarcosine oxidase is completely removed by subsequent hydrophobic chromatography on phenylsepharose.

In decreasing gradients of 20 mM/liter potassium phosphate buffer (pH 6.5) containing 1.0M/liter ammonium sulphate, to 20 mM/liter potassium phosphate buffer (pH 6.5) the CSH is eluted at about 0.4M/liter ammonium sulphate.

The eluate is dialysed cold against 20 mM/liter potassium phosphate buffer (pH 6.5) and applied to a column of DE-52-cellulose which has been equilibrated with the same buffer. The CSH is eluted by an increasing gradient with the above buffer of from 50 to 500 mM/liter sodium chloride. The eluate is concentrated by ultrafiltration.

After subsequent gel filtration in 0.1M potassium phosphate buffer (pH 6.5), using Sephacryl-S-200, the CSH is obtained in 53% yield, with a specific activity of 2.1 U/mg. The enzyme can be stored without loss of activity for more than 6 months in 50% glycerol solution, pH 6.5, at +4° C.

The following Table gives the details of the above-described purification process:

| Separation and purification of CSH from 1 kg. dry mass of Arthrobacter | | | | |
|---|---|---|---|---|
| step | protein in g. | CSH KU | U/mg. | yield % |
| cell digestion (extract) | 200 | 28 | 0.14 | 100 |
| cell fragments (emptied cells) | — | 0.5 | — | 1.7 |
| cell extract + G-35, 2nd precipitate | 54 | 27 | 0.50 | 96 |
| 1.3–2.2 M AS/ precipitate | 40 | 24 | 0.60 | 86 |
| phenylsepharose eluate | 13.8 | 22 | 1.60 | 79 |
| DE-52-cellulose eluate | 10 | 18 | 1.80 | 64 |
| end preparation after gel filtration | 7.1 | 15 | 2.10 | 53 |

EXAMPLE 3

From a culture batch of Moraxella DSM 2562 (BMTU 2913-1), cultured on N-methylhydantoin as described in Example 2a), there are obtained 180 g. of dry mass. The CSH is purified similarly to Example 1B). However, instead of by high pressure dispersion, the cells are lysed with 0.05% lysozyme (g./g. dry mass) at pH 7.0.

The following Table gives the details of the purification process:

| Isolation of CSH from 180 g. dry mass of Moraxella | | | | |
|---|---|---|---|---|
| step | protein in g. | CSH KU | U/mg. | yield % |
| cell lysis extract | 28.4 | 3.5 | 0.12 | 100 |
| cell fragments | — | — | — | — |
| cell extract + G-35, 2nd precipitate | 7.7 | 3.4 | 0.44 | 97 |
| 1.25–2.1 M AS/ precipitate | 5.7 | 3.3 | 0.58 | 94 |
| phenylsepharose eluate | 2.0 | 3.3 | 1.65 | 94 |
| DE-52-cellulose eluate | 1.2 | 2.5 | 2.1 | 71 |
| end preparation after gel filtration | 1.2 | 2.4 | 2.0 | 68 |

EXAMPLE 4

Determination of CSH with o-dianisidine

Principle:

N—carbamoylsarcosine + $H_2O$ $\xrightarrow{CSH}$ sarcosine + $CO_2$ + $NH_3$ sarcosine + $O_2$ + $H_2O$ $\xrightarrow{Sarc-OD}$ glycine + formaldehyde + $H_2O_2$ $H_2O_2$ + o-dianisidine $\xrightarrow{POD}$ coloured material + $2H_2O$ Solutions:
1. tris buffer 0.1 mol/l.; pH 8.0
2. o-dianisidine solution; 66 mg. o-dianisidine hydrochloride dissolved in 10 ml. of buffer (1)
3. test buffer: pipette 1.0 ml. solution 2 into 99 ml. solution 1 and mix. Can be kept for a week at +4° C.
4. peroxidase: dissolve 2 mg. POD (Boehringer Mannhsion Gmbol purity grade I) in 1 ml. water
5. sarcosine oxidase: dissolve 100 U/ml. purified sarc-OD (uricase- and catalase-free) in water
6. N—carbamoylsarcosine 0.25 mol/l.

Sample

Dilution with cold 50 mmol/liter KPO$_4$ buffer (pH 6.5)

Conducting of the assay 436 nm; 25° C.; V=2.00 ml.; d=1 cm.; ε=8.3 cm$^2$×μmol$^{-1}$

| Pipette into curvette | | |
| --- | --- | --- |
| buffer | (3) | 1.80 ml. |
| POD | (4) | 0.01 ml. |
| sarc-OD | (5) | 0.05 ml. |
| carbamoylsarcosine | (6) | 0.10 ml. |
| Mix, wait about 10 minutes, then start with sample | | |
| sample | | 0.04 ml. |
| mix, allow to proceed for 10 minutes and calculate ΔE/min. from the linear phase | | |

Calculation: $\frac{\Delta E/\min. \times 2 \times \text{dilution}}{8.3 \times \text{ml. of sample used}} = \text{U/ml.}$

We claim:

1. A process for the determination of N-carbamoylsarcosine in a sample, comprising
   reacting said sample with N-carbamoylsarcosine-amidohydrolase to give sarcosine; and determining the sarcosine formed as an indication that N-carbamoylsarcosine is present in the sample.

2. Process according to claim 1, wherein sarcosine is determined by reacting said sarcosine with oxygen in the presence of sarcosine oxidase and determining consumption of oxygen.

3. Process according to claim 2 wherein the reaction is carried out in buffered solution at a pH value of from 6 to 9.

4. Process according to claim 1, wherein the reaction is carried out in buffered solution at a pH value of from 6 to 9.

5. Process according to claim 1, wherein the amount of sarcosine is determined by reacting sarcosine with oxygen in the presence of sarcosine oxidase to form hydrogen peroxide, and determining the hydrogen peroxide as a measure of the sarcosine.

6. Substantially pure enzyme N-carbamoylsarcosine-amidohydrolase which catalyzes formation of sarcosine, carbon dioxide and ammonia from N-carbamoylsarcosine.

7. A process for obtaining an enzyme, N-carbamoylsarcosine-amidohydrolase, comprising culturing microorganisms containing said enzyme on a medium containing N-methylhydantoin and separating said N-carbamoylsarcosine-amidohydrolase from the culture.

8. Process according to claim 7 wherein there is used a micro-organisms of the genus Arthrobacter, Micrococcus or Moraxella.

9. Process according to claim 8, wherein the is used Arthrobacter DSM 2563, DSM 2564, Micrococcus spec. DSM 2565 or Moraxella DSM 2562.

10. Reagent for the determination of N-carbamoyl sarcosine comprising a mixture of N-carbamoylsarcosine-amidohydrolase, sarcosine oxidase, a compatible system for the detection of hydrogen peroxide, and a compatible buffer of from about pH 6 to about 9.

11. Reagent of claim 10, further comprising a compatible surface-active agent.

12. A kit for determination of N-carbamoyl sarcosine comprising individually packaged N-carbamoylsarcosine-amidohydrolase, sarcosine oxidase, a compatible system for detection of hydrogen peroxide, and a buffering agent of from about pH 6 to about 9.

* * * * *

UNITED STATES PATENT AND TRADEMARK OFFICE
CERTIFICATE OF CORRECTION

PATENT NO. : 4,645,739

DATED : February 24, 1987

INVENTOR(S) : Rolf Deeg, et al.

It is certified that error appears in the above-identified patent and that said Letters Patent is hereby corrected as shown below:

Column 2, line 56: change "hope" to -- hepes --.

Column 6, line 64: change "Mannhsion Gmbol" to -- Mannheim GmbH --.

Column 8, line 19: change "organisms" to -- organism --;
               line 21: change "the" to -- there --.

Signed and Sealed this

Fifth Day of January, 1988

Attest:

DONALD J. QUIGG

*Attesting Officer*        *Commissioner of Patents and Trademarks*